(12) United States Patent
Wu

(10) Patent No.: US 8,877,740 B2
(45) Date of Patent: Nov. 4, 2014

(54) COMPOUND COMPOSITION FOR INHALATION USED FOR TREATING ASTHMA

(75) Inventor: Wei-Hsiu Wu, Taipei (TW)

(73) Assignee: Intech Biopharm Ltd., Taipei (TW)

(*) Notice: Subject to any disclaimer, the term of this patent is extended or adjusted under 35 U.S.C. 154(b) by 1 day.

(21) Appl. No.: 13/876,387

(22) PCT Filed: Feb. 1, 2011

(86) PCT No.: PCT/CN2011/070883
§ 371 (c)(1),
(2), (4) Date: Oct. 8, 2013

(87) PCT Pub. No.: WO2012/041031
PCT Pub. Date: Apr. 5, 2012

(65) Prior Publication Data
US 2014/0031324 A1 Jan. 30, 2014

(30) Foreign Application Priority Data

Sep. 28, 2010 (CN) .......................... 2010 1 0502339

(51) Int. Cl.
| | | |
|---|---|---|
| *A01N 45/00* | (2006.01) |
| *A61K 31/53* | (2006.01) |
| *A61K 31/573* | (2006.01) |
| *A61K 9/00* | (2006.01) |
| *A61K 31/135* | (2006.01) |
| *A61K 31/137* | (2006.01) |
| *A61K 31/4704* | (2006.01) |
| *A61K 31/56* | (2006.01) |
| *A61K 31/58* | (2006.01) |
| *A61K 31/138* | (2006.01) |

(52) U.S. Cl.
CPC .............. *A61K 31/573* (2013.01); *A61K 9/008* (2013.01); *A61K 31/135* (2013.01); *A61K 31/137* (2013.01); *A61K 31/4704* (2013.01); *A61K 31/56* (2013.01); *A61K 31/58* (2013.01); *A61K 31/138* (2013.01)
USPC ....................................................... 514/171

(58) Field of Classification Search
None
See application file for complete search history.

(56) References Cited

U.S. PATENT DOCUMENTS

| | | | |
|---|---|---|---|
| 6,932,962 B1 | 8/2005 | Backstrom et al. | |
| 2007/0020190 A1* | 1/2007 | Razzetti et al. ................ | 424/45 |
| 2011/0251157 A1* | 10/2011 | Pipkin et al. ................... | 514/58 |

FOREIGN PATENT DOCUMENTS

| | | |
|---|---|---|
| CN | 1425378 | 6/2003 |
| CN | 101124198 | 2/2008 |
| CN | 101433527 | 5/2009 |

OTHER PUBLICATIONS

Yoshida et al. (Int Arch Allergy Immunol, Jul. 1, 2009, 150, 352-358).*
Petty et al. (American Review of Respiratory Disease, 1998, 138, 1504-1509) (Abstract Only).*

* cited by examiner

*Primary Examiner* — Anna Pagonakis
*Assistant Examiner* — Daniel M Podgorski
(74) *Attorney, Agent, or Firm* — Min-Lee Teng; Litron Patent & Trademark Office

(57) ABSTRACT

A compound composition for inhalation comprising β2 receptor agonist and corticosteriod is provided in the present invention. The composition is used as a reliever for a patient with asthma or chronic obstructive pulmonary disease, or a controller in eccentric way, and can reduce drug acute resistance of β2 receptor agonist.

8 Claims, 4 Drawing Sheets

Fig. 3

COMPOUND COMPOSITION FOR INHALATION USED FOR TREATING ASTHMA

CROSS REFERENCE TO RELATED APPLICATIONS

This application claims the priority of Chinese Patent Application 201010502339.3, filed on Sep. 28, 2010, which is incorporated by reference as if fully set forth herein in its entirety.

This application is a 35 U.S.C. §371 national phase application of PCT/CN2011/070883, which was filed Feb. 1, 2011 and is incorporated herein by reference as if fully set forth.

FIELD OF THE INVENTION

The present invention relates to a pharmaceutical composition of compounds, in particular to the composition which contains an inhaled corticosteroid combined with a short (rapid) acting beta-2 agonist.

BACKGROUND OF THE INVENTION

Inhaled medicines for treating Asthma or Chronic Obstructive Pulmonary Disease, COPD, is preferred than oral dosage form product because they delivers medication directly to the target acting site, hence the given dose is minimized and the systemic side effects are reduced. Most commonly used inhaled medicines include inhaled corticosteroids, beta-2 agonists, anticholinergics, or combinations of the above medicine.

Commercially available inhaled corticosteroid includes Fluticasone propionate, Budesonide, Ciclesonide, Mometasone furoate, Beclomethasone dipropionate, Triamcinolone acetonide, and Tipredane, etc. Due to the anti-inflammatory action, they were used as controller in asthma or COPD treatment either administer alone or combined with long acting beta-2 agonist (LABA).

Commercially available beta-2 agonists include Albuterol sulfate (also called Salbutamol sulphate), Procaterol hydrochloride, Fenoterol hydrocromide, Reproterol hydrochloride, Formoterol, Terbutaline sulphate, and Salmeterol xinafoate.

Both Formoterol and Salmeterol are long acting beta-2 agonists (LABA) with duration of action up to twelve hours. In practice, LABA is suggested to be combined with inhaled corticosteroid and given twice daily to act as controller in patients with moderate to severe Asthma. The reason why LABA is not suggested to be used alone in asthma is that it will develop tolerance through beta-2 receptors down regulation which will results reduced efficacy or even higher exacerbation rate or deaths under routine treatment if used alone. While inhaled corticosteroid could reduce beta-2 receptors' down regulation, consequently reduce the extent of beta-2 agonists' tolerance, hence was suggested to combine with LABA as controller for asthma's long term treatment.

Fenterol, Aalbuterol, Terbutaline, or Procaterol are short acting beta-2 agonist (SABA) with the duration of action between 3 to 6 hours or 4 to 8 hours. In clinical application, SABA is mainly used alone as needed to relieve the status of acute bronchoconstriction, if necessarily, it can be used thrice to four times a day. In the prior art, there are several related patent allocation, such as: 1). the Taiwan application No. 200303767 discloses that the superfine formula of Formoterol contains 0.003-0.192% w/v of (R,R)-(±)-Formoterol fumarate; 2). the Taiwan patent No. 329837 discloses a pharmaceutical composition containing Mometasone furoate for treating airway disease and lung disease; 3). the China application No. CN1305380 discloses a composition including Formoterol and Budesonide for applying on preventing and treating acute asthma; 4). the U.S. Pat. No. 5,972,919 disclose a formulation containing an effective amount Formoterol and Budesonide and the molar ratio of the content is 1:4 to 1:70, 5). the U.S. Pat. Nos. 6,932,962, 6,799,572, 6,638,495, 6,962, 151 and U.S. Pat. No. 7,321,059 have disclosed a combination about inhaled corticosteroids, which is one selected from Budesonide, Fluticasone, Mometasone, Beclomethasone, or Ciclesonide, etc. and Beta-2 agonist which is one selected from Fenoterol, Albuterol, Procaterol, Salmeterol, or Formoterol, etc. and 6). the U.S. Pat. Nos. 7,244,742, 7,481,995, and U.S. Pat. No. 6,596,261 further discloses that the compound of inhaled corticosteroids collocating with beta-2 agonists is added to Anticholinergics of Ipratropium. However, what recited in the above-mentioned references are all about techniques of Pharmaceutical formulation, and it is not what disclosed by the present invention that using combinations of acting time, dosage, and usage to improve clinical performances.

Austria et al. disclose that a control therapy by adding low or high dosage of inhaled Budesonides to oral Procaterol for treating patients between 7 to 18 year-old and found under regular asthma treated by Procaterol and Budesonide (Chest, 2005) can improve the asthma condition. However, the numbers of patients are too few, and there is no difference between the low dosage and the high dosage. In addition, on Apr. 4, 2010, Japan disclosed that using 15 to 30 mcg inhaled solution of Procaterol and 250 mcg inhaled suspension of Budesonide on a nebulizer twice a week, after one week, switch to use Budesonide alone for treating regular asthma of teenagers. The above two respiratory therapies are using oral beta-2 agonists to combined with inhaled corticosteroids or using a nebulizer to continuously spray these two medicines, and the above-mentioned respiratory therapies are different from the metered dose inhaled combination product or dry-powder inhalation of the present invention. Furthermore, when the drug delivered through nebulizing solution, patients need to inhale the medicine for a period of 10 to 15 minutes, hence, the drug amount given to the patients are much higher than administered from the metered dose inhaler or the Dry-powder inhaler, and in addition they were all given twice daily as control therapy. Therefore, they are different from the present invention in partial polarity control therapy (eccentric therapy) in order to provide a drug blood concentration variation within a day to meet the need of daily lung function circadian rhythm changes.

Respiratory diseases such as asthma and chronic obstructive pulmonary disease (COPD) are caused by urbanization with environmental pollution problems. Such respiratory diseases have become one of the major diseases of globalization. Most research findings show that the high asthma mortality is related to low diagnosis rates and treatment inadequate. In 1993 World Health Organization and the National Institutes of Health invited experts to discuss control solutions of asthma and organized the Global Initiative for Asthma, GINA, which is an ongoing council organization. Every few years, based on medical evidences, the organization constantly updates treatment concepts with new clinical evidences and writes the latest asthma treatment guidelines for national health care information.

Now, GINA treatment guidelines is currently suggesting a step up or step down treatment options based on patient's status of control:

1. Step 1: For most mild asthma patients: Reliever medicine such as rapid short-acting β2-agonists is given as needed for quick relieve of symptoms;
2. Step 2: For mild asthma patients:
   A, controller: a. give low dose inhaled corticosteroids or
      b. leukotriene inhibitors.
   B, reliever: When asthma attack, rapid short-acting β2-agonists was given as needed;
3. Step 3: For moderate asthma patients:
   A, controller: Selectively give
      a. "low-dose inhaled cortico steroids plus long-acting beta-2 agonists",
      b. medium to high-dose inhaled corticosteroids,
      c. "low-dose inhaled corticosteroids plus Leukotriene modifiers", or
      d. "low-dose inhaled cortico steroids plus sustained released theophylline."
   B, reliever: When asthma attack, rapid short-acting β2-agonists was given as needed;
4. Step 4: for severed asthma patients:
   A, controller: to step 3 treatment: select one or more from
      a. "medium to high-dose inhaled corticosteroids plus long-acting beta-2 agonists",
      b. leukotriene modifiers,
      c. sustained released theophylline.
   B, reliever: When asthma attack, rapid short-acting β2-agonists was given as needed;
5. Step 5. The severe acute-exacerbation:
   A, control treatment: to step 4 treatment add either oral corticosteroids or anti-IgE immunotherapy,
   B, reliever: When asthma attack, rapid short-acting β2-agonists was given as needed;

From the publications, we know that although beta-2 agonists have a bronchodilating effects, but either short-acting or long-acting beta-2 agonist is not recommended to be used alone to treat patients as controller. The reason was when given higher frequent or higher doses, it will develop acute tolerance (Tachyphylaxis) phenomena, under which, the dose given to the patients need to be increased rapidly to achieve the same therapeutic effect, or sometimes cause the loss of efficacy, or make the patient more vulnerable to asthma attack. Therefore, Tachyphylaxis phenomena might increase the acute exacerbations, hospitalization, and mortality of patients.

Generally it is believed that the acute tolerance of beta2-agonists' result from β2 receptors down regulation under routine beta2-agonist treatment. Besides, it is known that some genotype patients are more vulnerable to develop acute tolerance under beta2-agonist treatment. Nowadays, it is well know that the inhaled corticosteroids can improve the β-2 receptor down regulation phenomenon, and this is why the combination of inhaled corticosteroids and long-acting beta2-agonist given every twelve hours effects is the main current medications for treating Asthma, such as Budesonide plus Formoterol fumarate, Fluticasone propionate plus Salmeterol xinafoate, Fluticasone propionate plus Formoterol fumarate, Ciclesonide plus Formoterol fumarate, Mometasone furoate plus Formoterol fumarate, Beclomethasone plus Formoterol fumarate, or Fluticasone furoate plus Vilanterol trifenatate etc. The dosage form of the above mentioned combination are mainly DPI (Dry Powder Inhaler), or MDI (Metered Dose Inhaler), and such pharmaceutical compositions of these combination have become the main stream of research and development currently.

These combination products contained long acting beta2-agonist and intend to give patients a 24 hours cover of blood concentration, such as Formoterol fumarate and Salmeterol xinafoate, were given twice a day to maintain 24 hours effects, and a 24 hours longer-acting drug Vilanterol trifenatate is given once a day.

Papi, A. et al, in 2007, disclosed a combination composition of Beclomethasone and short-acting agonist, Albuterol, is used for treating mild asthma as controller and it was given twice a day therapy.

In addition to the above-mentioned references, there still are U.S. Pat. Nos. 5,270,305, 5,658,549, 5,674,472, 5,674,860, 6,123,924, 6,143,277, 6,251,368, 6,253,762, 6,315,173, 6,510,969, 6,524,555, 6,546,928, 6,641,800, U.S. Pat. No. RE40045 and U.S. Pat. No. 7,067,502 and U.S. pub. No. 20100008997, No. 20090274771, No. 20090258075, No. 20090047336, No. 20080279788, No. 20080078382, No. 20080066741, No. 20080066739, No. 20070196285, No. 20060054166, No. 20050085445, No. 20040241103, No. 20040105819 and No. 20040101483. Although they disclose many of the "inhaled corticosteroid mixing with beta2-agonist" of the formulation technology or drug delivery technology inventions, but none of them taught about the inhaled corticosteroid mixing with the rapid effects of moderately short-acting beta2-agonist such as Procaterol HCl, etc., and the method of using such combination.

In U.S. patent database, there are patents disclose the beta2-agonist, Procaterol HCl, used with the inhaled corticosteroid, such as U.S. Pat. Nos. 6,503,537 7,387,794 involving in the preparation of powder of agglomerates; U.S. Pat. Nos. 7,244,414, 7,658,949, 7,687,073, 7,694,676 7,736,628 involving in the dry powder inhaler; U.S. Pat. No. 7,172,752 involving in combination particles; U.S. Pat. No. 7,550,133 related to respiratory drug condensation aerosols; U.S. Pat. No. 7,109,247 for particles dispersions containing nanoparticles; U.S. Pat. No. 6,814,953 related to a nebulized aerosol; U.S. Pat. No. 6,932,962 related to an aerosol drug containing hydrofluoroalkanes and alkyl saccharides, HFA; U.S. Pat. No. 7,244,742 related to adding anti-cholinergic drugs; U.S. Pat. No. 7,267,813 containing crystalline spherical inhalation particles; U.S. Pat. No. 7,459,146 related to using for modified polyethylene glycol, PEG, nanoparticles HFA inhalation aerosol propellants. And what mentioned above is not same as the present invention.

References have also showed that the adding of the inhaled corticosteroid only alleviates part of acute drug tolerance phenomenon of the beta2-agonist. In our research, we also found that when the beta2-agonist was given too high single dose, it will produce an acute drug tolerance. This reveals that there are reasons other than beta2 receptor downregulation to cause the acute tolerance.

According to the relevant references, the mechanism of beta2-agonist's tachyphylaxis may be related to the exhaust of some endogenous trachea-relaxing substances which mediate trachea relaxation. Such as substantially increased intracellular cyclic adenosine monophosphate (cAMP) concentrations after administration of beta2-agonist. The released cAMP is catalyzed by proteases and generates serial reactions to relax the trachea. Therefore, when given a large amount or high frequency of beta2-agonist, the endogenous trachea-relaxing substances will be exhausted simultaneously. When the internal recovery rate of these substances is less than the consumption, it might induce the acute drug tolerance phenomenon.

It is also well know that asthma patient's lung functions will change during a day. Due to the neurohormonal circadian change, the lung function is the worst at 04:00 am and is the best at 16:00 pm. Based on the circadian rhythm of the lung function and the above-mentioned mediating substance exhausted mechanism, the inventor proposed a new way of therapy to asthma or chronic pulmonary obstruction. After carefully testing and research with a spirit of, and a spirit of perseverance, the inventor eventually has proposed an invention, "Inhaled Combination Product for Asthma." The summary of the present invention is described as follows.

SUMMARY OF THE INVENTION

The present invention provides an inhaled composition combination which contains an effective amount of beta2-agonist and an effective amount of inhaled corticosteroid. When it is necessary, it can include a pharmaceutically acceptable carrier.

The present invention further provides an inhaled metered dose aerosol or powder inhalator combination which contains an effective amount of beta2-agonist and an effective amount of inhaled corticosteroid. When it is necessary, it can include a pharmaceutically acceptable carrier.

According to the above-mentioned aspect of the present invention, the so called beta2-agonist is selected from short or fast acting beta2-agonists such as Albuterol, Fenoterol, Procaterol, terbutaline, Albuterol sulfate, Procaterol HCl, Fenoterol hydrobromide and terbutaline sulphate.

According to the above-mentioned aspect of the present invention, the corticosteroid is selected from Budesonide, Fluticasone, Mometasone, Ciclesonide, Beclomethasone, Triamcinolone, Tipredane, Fluticasone propionate, Beclomethasone dipropionate, Triamcinolone Acetonide and so on.

According to the above-mentioned aspect of the present invention, one purpose of the present invention, "Inhaled Combination Product For Asthma," is using for eccentric way control therapy of asthma or chronic pulmonary obstruction diseases. Based on the above-mention circadian change of pulmonary function of asthma patients, the so called eccentric therapy by giving medicines before go to bed and after wake up, might be a better treatment option for patients' long term treatment. The eccentric treatment gives higher drug concentration during the worse stage of lung function and giving a lower concentration or drug free period during the better lung function stage during a day. Therefore, patients' body will have time to recover and accumulate the endogenous trachea-relaxing substances. In addition, such eccentric therapy could also use the same combination medicine as reliever to a patient with asthma or chronic pulmonary obstruction diseases when it is necessary. Thus, compared with the current control that patients are administered long-acting beta-2 receptor agonist compound drugs twice a day, the eccentric therapy could be a better treatment choice.

BRIEF DESCRIPTION OF THE DRAWINGS

FIG. 3 the bar chart shows the dose and the effect of the moderately long-acting beta2-agonist, Procaterol.
A: normal control group;
B: Asthma control group;
C: Procaterol 0.5 μg/kg, single dose;
D: Procaterol 0.5 μg/kg, twice daily×7 days;
E: Procaterol 1.0 μg/kg, single dose;
F: Procaterol 1.0 μg/kg, twice daily×7 days;
G: Procaterol 1.5 μg/kg, single dose;
H: Procaterol 1.5 μg/kg, twice daily×7 days;
I: Procaterol 2.5 μg/kg, single dose;
J: Procaterol 2.5 μg/kg, twice daily×7 days;
K: Procaterol 5.0 μg/kg, single dose;
L: Procaterol 5.0 μg/kg, twice daily×7 days;
M: Procaterol 10.0 μg/kg, single dose;
N: Procaterol 10.0 μg/kg, twice daily×7 days;
### is represented that compared with the normal control group, $p<0.001$;
* is represented that compared with the asthma control group, $p<0.01$.

Figure 1:
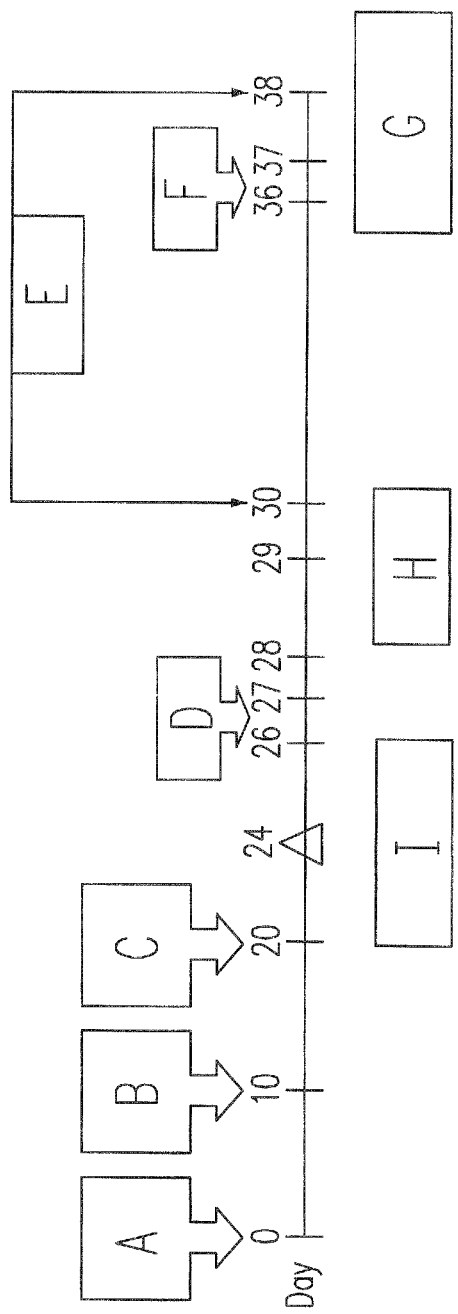
FIG. 1 the flow chart of the experiment.
A. 100 μg Ovalbumin is intraperitoneally injected (OVA 100 μg i.p.);
B. 50 μg Ovalbumin is intraperitoneally injected (OVA 50 μg i.p.);
C. 50 μg Ovalbumin is intraperitoneally injected (OVA 50 μg i.p.);
D. Nasal administration of ovalbumin is performed (OVA i.n.);
E. Intratracheal administration (I.T.) is performed once a day.
    After 7 days, airway hyperresponsiveness (AHR) is examined and bronchioalveolar lavage fluid (BALF) is used to observe an amount of immune cells and types changing (I.T. 7 Days AHR BALF);
F. OVA challenge i.n. (Nasal administration of ovalbumin is re-performed to ensure that mice are allergic);
G. Intratracheal administration (I.T.) is performed twice daily.
    After 7 days, airway hyperresponsiveness (AHR) is examined and bronchioalveolar lavage fluid (BALF) is used to observe an amount of immune cells and types changing (I.T. 7 Days twice daily);
H. After intratracheal administration (I.T.) is performed once a day.
    Airway hyperresponsiveness (AHR) is examined and bronchioalveolar lavage fluid (BALF) is used to observe an amount of immune cells and types changing (I. T. 1 Day AHR BALF);
I. IgE ELISA assay (the concentration of immunoglobulin E is examined by combining enzymes and ELISA to ensure the OVA-sensitized mice are established).

H: Budesonide 27.0 µg/kg with Procaterol 1.5 µg/kg, twice daily×7 days;

I: Budesonide 45.0 µg/kg with Procaterol 2.5 µg/kg, single dose;

J: Budesonide 45.0 µg/kg with Procaterol 2.5 µg/kg, twice daily×7 days;

K: Budesonide 90.0 µg/kg with Procaterol 5.0 µg/kg, single dose;

L: Budesonide 90.0 µg/kg with Procaterol 5.0 µg/kg, twice daily; ×7 days

M: Budesonide 180.0 µg/kg with Procaterol 10.0 µg/kg, single dose;

N: Budesonide 225.0 µg/kg with Procaterol 12.5 µg/kg, twice daily×7 days;

O: Budesonide 540.0 µg/kg with Procaterol 30.0 µg/kg, once daily×7 days;

P: Budesonide 900.0 µg/kg with Procaterol 50.0 µg/kg, single dose;

### is represented that compared with the normal control group, $p<0.001$;

** is represented that compared with the asthma control group, $p<0.01$;

*** is represented that compared with the asthma control group, $p<0.001$.

REFERENCES

Papi, A., G. W. Canonica, et al. (2007). "Rescue Use of Beclomethasone and Albuterol in a Single Inhaler for Mild Asthma." New England Journal of Medicine 356(20): 2040-2052.

Albers M, Schermer T, Van W C. Airflow limitation as a screening tool: too relevant to ignore, too conspicuous to apply? Chest 2005; 128(4):1898-900.

CHEST/128/4/October, 2005 Supplement

DETAILED DESCRIPTION OF THE PREFERRED EMBODIMENT

In order to understand the acute drug tolerance resulted from high dose and high frequency use of beta2-agonists, and to observe the effect of adding the corticosteroid to treatment. An albumin-inducing asthma model in mice was used to conduct related tests. The experimental procedure is shown in Table 1. In accordance with the control group and the experimental group, the mice were divided into the different groups to conduct the experiment. The control group includes a normal control group which none sensitized mice are given saline (no drug), and an asthma control group which sensitized mice are treated with vehicle. The experimental group is divided into sub-group according to different methods of administering drugs. Respectively, such as the group which is using different dosage and different frequency of the beta2-agonist alone and the group which is using different dosage and different frequency of the pharmaceutical combination of the beta2-agonist with the corticosteroid.

The mice which are for sensitization all experience three times of the peritoneal albumin (OVA) injection with ten-day intervals in advance, on the $24^{th}$ day, collect the blood sample and exam the IgE to confirm allergy. Then, on the $26^{th}$ day, albumin was administered in the nasal cavities of the mice. And, from the $30^{th}$ day, the intratracheal administration is divided into groups of once time dosing and seven-day dosing which is further divided into once or twice daily groups. After the last dose, perform a tracheotomy and intubation and use instruments collect the data of that Methacholine (MCh), induces tracheal contraction. In order to understand the alleviating effects of the present invention, pharmaceutical composition, compare with that the sensitized mice are given long-active or short-acting beta2-agonist alone (Salmeterol or Procaterol), and compare with the reaction of the normal mice and the control group.

Figure 2:
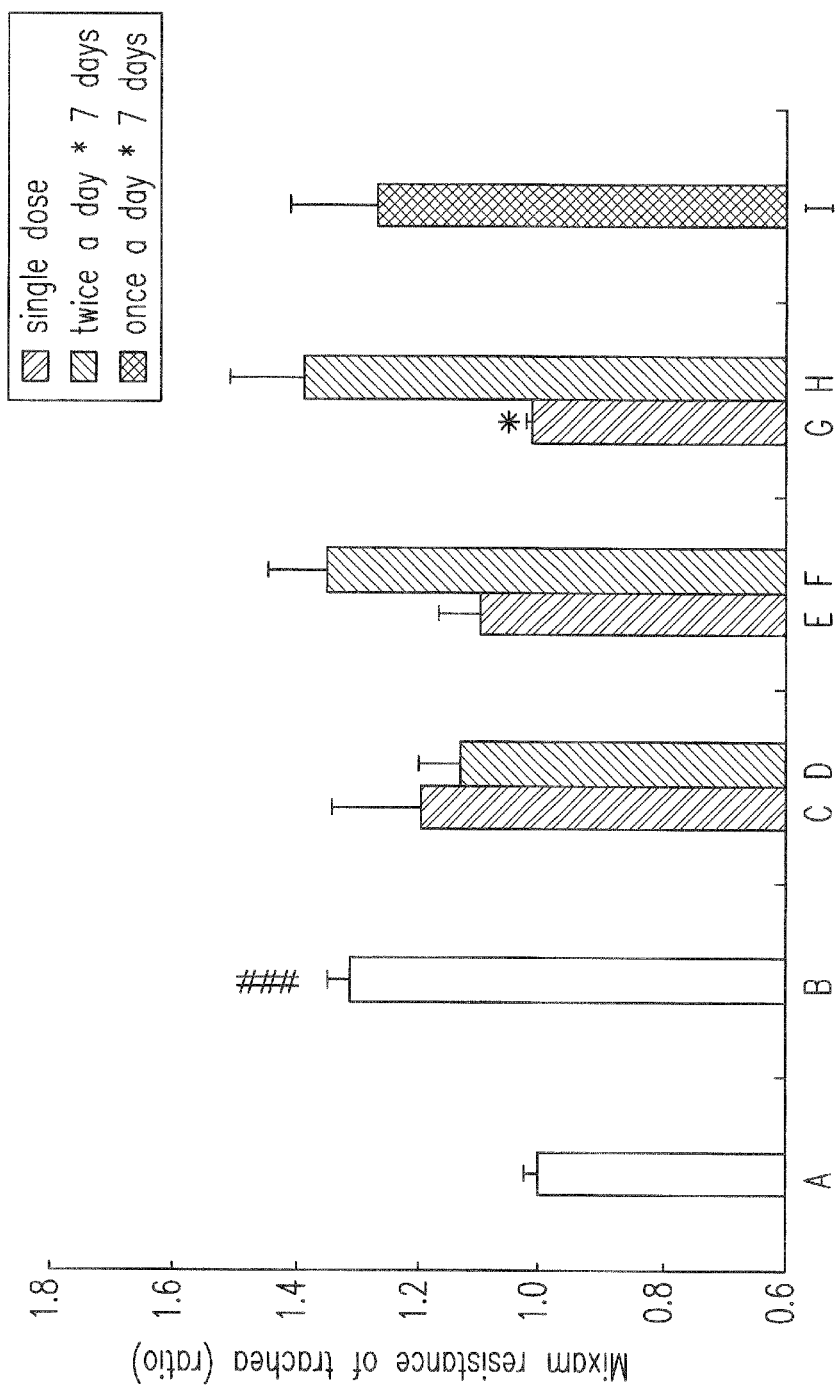
FIG. 2 the bar chart shows the dose and the effect of the long-acting beta2-agonist, Salmeterol.
A: normal control group;
B: Asthma control group;
C: Salmeterol Xinafoate 50.0 μg/kg, single dose;
D: Salmeterol Xinafoate 50.0 μg/kg, twice daily×7 days;
E: Salmeterol Xinafoate 200.0 μg/kg, single dose;
F: Salmeterol Xinafoate 200.0 μg/kg, twice daily×7 days;
G: Salmeterol Xinafoate 500.0 μg/kg, single dose;
H: Salmeterol Xinafoate 500.0 μg/kg, twice daily×7 days;
I: Salmeterol Xinafoate 500.0 μg/kg, once daily×7 days;
### is represented that compared with the normal control group, $p<0.001$;
* is represented that compared with the asthma control group, $p<0.05$.
Figure 3:
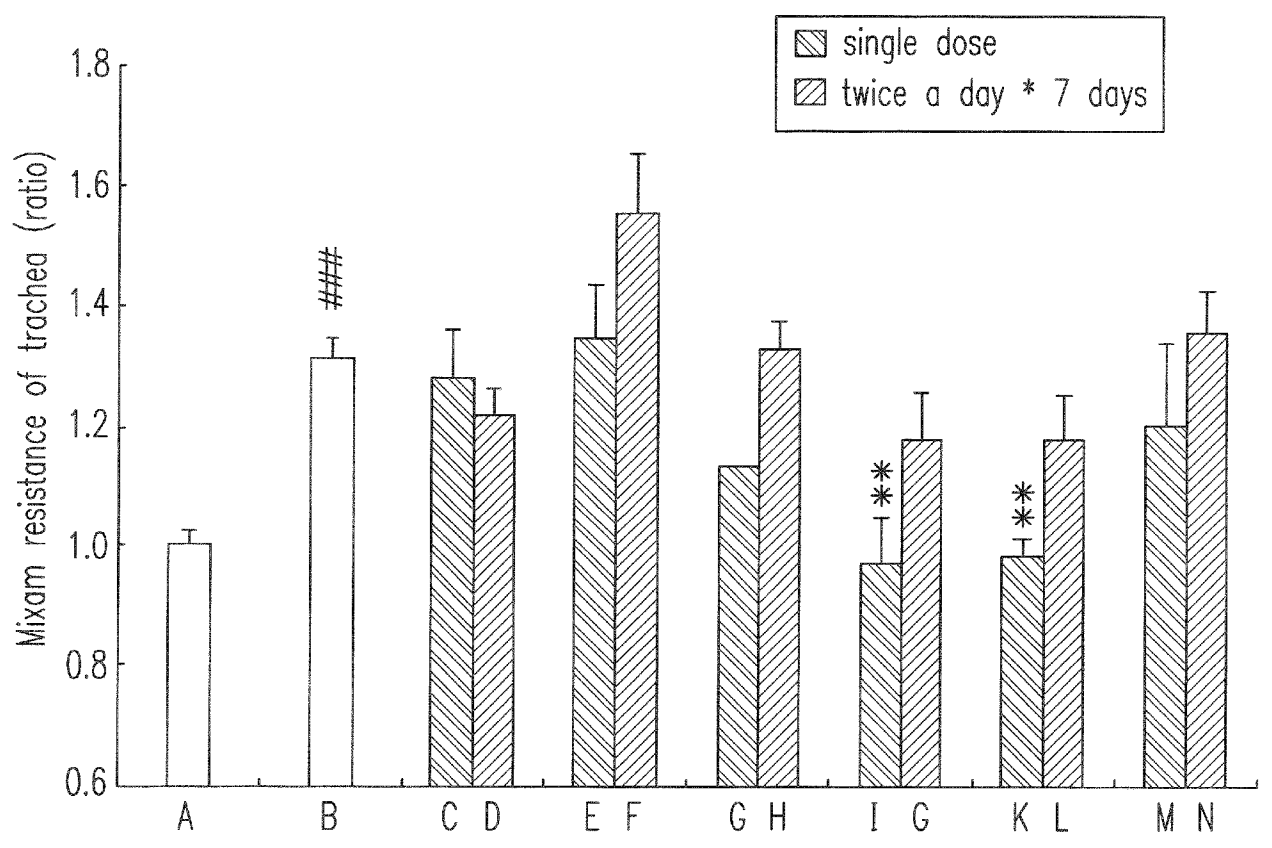
Figure 4:
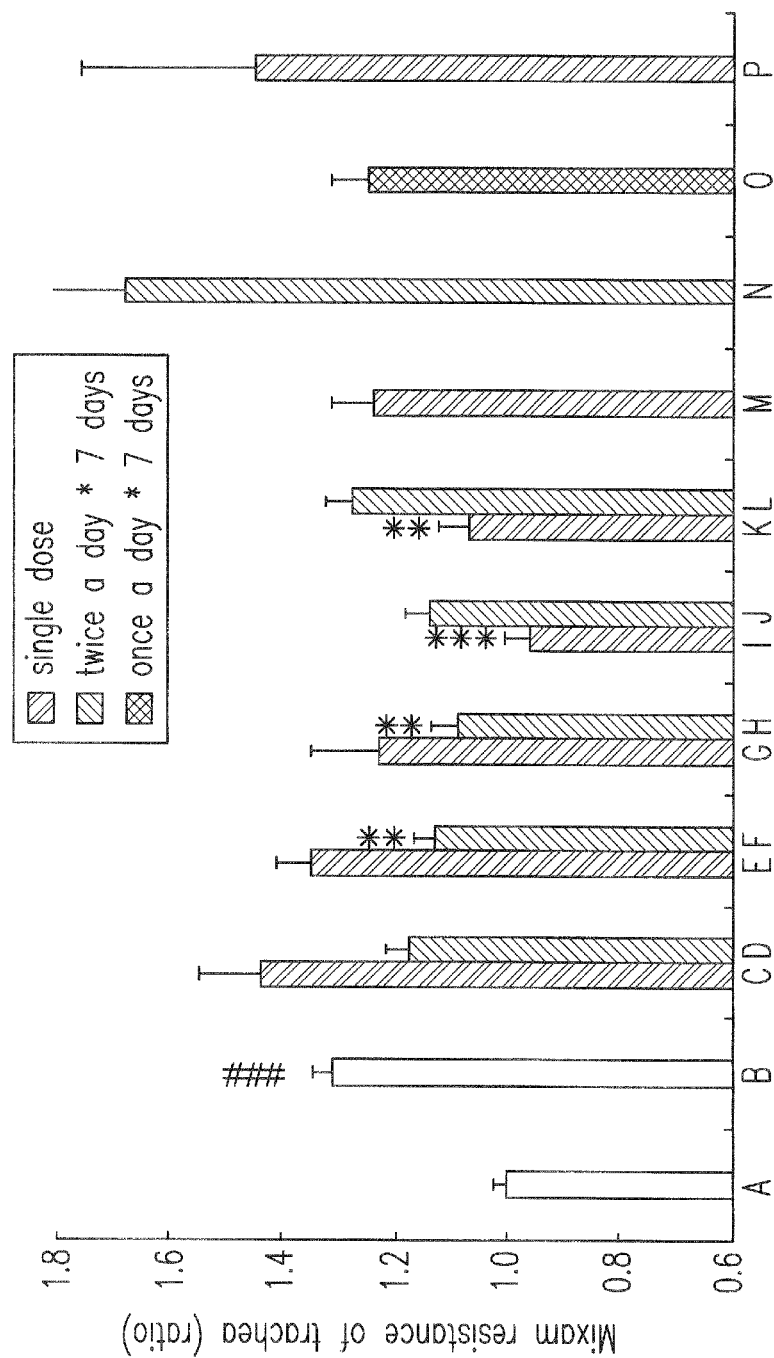
FIG. 4 the bar chart shows the dose and the effect of the composition, Budesonide mixing with Procaterol.
A: normal control group;
B: Asthma control group;
C: Budesonide 9.0 μg/kg with Procaterol 0.5 μg/kg, single dose;
D: Budesonide 9.0 μg/kg with Procaterol 0.5 μg/kg, twice daily×7 days;
E: Budesonide 19.0 μg/kg with Procaterol 1.0 μg/kg, single dose;
F: Budesonide 19.0 μg/kg with Procaterol 1.0 μg/kg, twice daily×7 days;
G: Budesonide 27.0 μg/kg with Procaterol 1.5 μg/kg, single dose.

The results are shown as in FIGS. 2 to 4, no matter administrating alone or administering in combination of the long-acting Salmeterol or medium-short-acting Procaterol, when giving a single super high dose can both make the sensitized mice to show an acute drug tolerance phenomenon of reducing the ability of trachea relaxing. The result shows that there is a suitable dose range for displaying medical effects. Administering the beta2-agonist twice daily cannot avoid the phenomenon of the acute tolerance, giving the inhaled corticosteroid, Budesonide, under a suitable dose range can help to relieve the acute drug tolerance. However, when using too high dose of the beta2-agonist, Budesonide cannot relieve the acute drug tolerance, and it shows that the dosage of the beta2-agonist has exceeded body affordability. These results also indirectly proved that the present invention proposes an idea and assumption that "an acute drug resistance results from exhaustion of endogenously trachea-relaxing substances.

Relative to the listed suggestions of GINA guidelines, it is suggested to use short-acting beta2-agonist alone as reliever for treating emergent exacerbation of all kind of patients. If swapping the administering way of the short-acting beta2-agonist to another administering way by using a combination inhaler of the short-acting beta2-agonist with the inhaled corticosteroid, i.e., using the present invention which is a combination of inhaled corticosteroid with medium-short acting beta2-agonist for all level patients with emergent exacerbations as reliever, it might help the patient's recover from their asthma exacerbations.

From the fact that, when the step 5 patients under severe exacerbation, they need to use additional oral corticosteroid to control their acute asthma exacerbations, we can see that the patients may require additional corticosteroids to help patients to restore the relaxing functions of trachea by control the inflammation, counteract the beta2-receptor down regulation and help to restore the level of tracheal relaxing mediator.

Regarding to the related researches, only the reference which sponsored by Chiesi published on New England Journal of Medicine 2007; 356: 2040-2052 involves a research of inhaled corticosteroids with rapidly short-acting beta2-agonist. The result indicates that after six months treatment in mild asthma patients, the as needed (which means does not give drugs until exacerbations of asthma) administration of combination of Beclomethasone and Albuterol, shows that, compared with using Albuterol alone, the disease status is controlled better, acute exacerbation and hospitalizations were also reduced. Although this study only discussed the situation in patients with mild asthma, and not in moderately to severe patients under the conventional control medicine, it revealed that when the patients have exacerbations, beside the beta2-agonist, giving more corticosteroid is helpful for controlling the condition of disease.

Therefore, the present invention which is a compound of corticosteroid with rapidly short-acting beta2-agonist which can offer a better choice for using as an reliever for treating acute bronchial constriction of asthma in all levels patents. Such extra corticosteroids given can provide extra anti-inflammatory effect to assist patients to relieve from disease condition earlier.

In accordance with composition of the formula of the present embodiment, medium-short acting beta2-agonist are used, such as Procaterol, Fenoterol, Terbutaline, Albuterol and its base drugs, which has bronchodilating actions of 6 to 8 hours. If the above medicine was administrated 3 to 4 times a day, the phenomenon of acute tolerance will be produced rapidly, and the duration of bronchodilating effect will be reduced to 3 to 4 hours. Use the medium-short acting beta2-agonist together with an inhaled corticosteroid, such as budesonide, and adapting an eccentric way of before sleeping and after awake can restore duration of action back to 6 to 8 hours. Therefore, the present invention can help the long-term control of patients' disease and reducing the acute exacerbation.

The beta2-agonist with 3 to 8 hours duration, such as Procaterol HCl, Procaterol, Albuterol, Albuterol sulfate, Fenoterol, and Fenoterol hydrobromide etc. was use to combined with inhaled corticosteroid, such as Budesonide, Fluticasone, Beclomethasone, Mometasone, Ciclesonide, Triamcinolone and their base morphology, generate a quantitative combination metered dose inhaler or a dry powder inhaler. The weight ratio of the beta2-agonist and the inhaled corticosteroid is about 1:2 w/w % to 1:70 w/w %, and the better range is about 1:5 w/w % to 1:60 w/w %.

The clinical usage is giving the combination drug to asthma patients as controller before sleeping and after waking up. The advantage is to provide patients' body a low dose period to recover trachea relaxing mediators for the next day treatment during their better lung function period in the afternoon. Hence, it reduces the chance of acute tolerance of the beta2-agonist and help patients to control their conditions stably.

Compared with using short-acting beta2-agonist (Procaterol, Albuterol, Terbutaline, Fenoterol and its base drugs) alone, the combination has additional anti-inflammatory inhaled corticosteroid. The inhaled corticosteroid provided the anti-inflammatory and mitigation of the acute tolerance resulting from overuse of beta2-agonist, it can help to relieve conditions and reduce numbers of severe exacerbations.

The present invention which is an eccentric treatment of the combination of inhaled beta2-agonist with corticosteroid and can be administered via HFA MDI or DPI (dry powder inhaler). The above-mentioned pharmaceutically acceptable vectors are provided as an excipient system for need of preparing the combination product of the beta2-agonist with the corticosteroid, so it makes the administered animals or humans not to have adverse reactions, allergies or other non-appropriate responses. Carriers or an excipient system can also include the proper amount of surface active agents, solvents, suspending agents and propellants for stabilizing prescriptions. The formulation of HFA MDI used in the present invention is usually adopted 1,1,1,2-tetrafluoroethane (Tetrafluoroethane, HFA 134a, HFC 134a) or 1,1,1,2,3,3,3-Heptafluoropropane (Heptafluoro-n-propane, HFC 227ea, HFC 227, HFA 227), and depending on necessity, it can also be a mixture formulation of HFA 134a and HFA 227. Dry powder inhalation could be a single dose inhaler or multiple dose inhaler composed of carrier-free active pharmaceutical ingredients or use lactose as a carrier.

Experimental Methods:

Balb/c mice are divided into normal control group, asthma control group (Ova control group), and each group which is contained 2 to 28 mice (in the pre-exploration stage, the number of the mice is fewer, and in the post stage after confirming dose, the number of the mice for repeatedly confirming experiments is more) is supplied with the same water and food. In the asthma control group, at first, the mice are received i.p. with ovalbumin (OVA) with the interval of 10 days as shown in FIG. 1, and the mice are made to have allergies, on the 24th days, the blood are collected from the eye sockets of the mice to be examined by IgE Elisa quantification for confirming that the mice have allergies. In the normal control group, the mice are not made to have allergies and are given salt water. In the asthma control group, the mice are also given salt water but not medicine for treating, and 3 days before administration, the mice are continuously given OVA in the nasal to enhance allergies.

The mice of each group are divided into subgroups by different medicine and different dose. Each subgroup is divided into single administration within 7 days (one dose), once administration a day for 7 days (qd) or twice administrations a day (bid) for 7 days. The salt water or mixture drug of Procaterol mixing with Budesonide in the salt water is directly administered in the throats of the mice.

TABLE 1

| group/subgroup/code | administering way | Number of mice |
| --- | --- | --- |
| Normal control group | Single dose | 18 |
|  | Twice a day × 7 days | 19 |
| Ova control group | Single dose | 21 |
|  | Once a day × 7 days | 14 |
|  | Twice a day × 7 days | 28 |
| Budesonide 9.0 µg/kg with Procaterol 0.5 µg/kg (B9 + P0.5) | Single dose | 7 |
|  | Twice a day × 7 days | 13 |
| Budesonide 19.0 µg/kg with Procaterol 1.0 µg/kg (B19 + P1) | Single dose | 11 |
|  | Twice a day × 7 days | 19 |
| Budesonide 27.0 µg/kg with Procaterol 1.5 µg/kg (B27 + P1.5) | Single dose | 6 |
|  | Twice a day × 7 days | 12 |
| Budesonide 45.0 µg/kg with Procaterol 2.5 µg/kg (B45 + P2.5) | Single dose | 8 |
|  | Twice a day × 7 days | 15 |
| Budesonide 90.0 µg/kg with Procaterol 5.0 µg/kg (B90 + P5) | Single dose | 10 |
|  | Twice a day × 7 days | 25 |
| Budesonide 180.0 µg/kg with Procaterol 10.0 µg/kg (B180 + P10) | Single dose | 10 |
| Budesonide 200.0 µg/kg with Procaterol 12.5 µg/kg (B200 + P12.5) | Once a day × 7 days | 3 |
| Budesonide 225.0 µg/kg with Procaterol 12.5 µg/kg (B225 + P12.5) | Twice a day × 7 days | 2 |
| Budesonide 540.0 µg/kg with Procaterol 30.0 µg/kg (B540 + P30) | Once a day × 7 days | 2 |
| Budesonide 900.0 µg/kg with Procaterol 50.0 µg/kg (B900 + P50) | Single dose | 2 |
| Procaterol 0.5 µg/kg (P0.5) | Single dose | 7 |
|  | Twice a day × 7 days | 12 |
| Procaterol 1.0 µg/kg (P1) | Single dose | 13 |
|  | Twice a day × 7 days | 10 |
| Procaterol 1.5 µg/kg (P1.5) | Single dose | 7 |
|  | Twice a day × 7 days | 15 |
| Procaterol 2.5 µg/kg (P2.5) | Single dose | 5 |
|  | Twice a day × 7 days | 9 |
| Procaterol 5.0 µg/kg (P5) | Single dose | 5 |
|  | Twice a day × 7 days | 14 |
| Procaterol 10.0 µg/kg (P10) | Single dose | 5 |
|  | Twice a day × 7 days | 10 |

TABLE 1-continued

| group/subgroup/code | administering way | Number of mice |
|---|---|---|
| Salmeterol Xinafoate 50.0 μg/kg (S50) | Single dose | 5 |
| | Once a day × 7 days | 2 |
| | Twice a day × 7 days | 8 |
| Salmeterol Xinafoate 100.0 μg/kg (S100) | Once a day × 7 days | 3 |
| Salmeterol Xinafoate 200.0 μg/kg (S200) | Single dose | 6 |
| | Once a day × 7 days | 6 |
| | Twice a day × 7 days | 9 |
| Salmeterol Xinafoate 500.0 μg/kg (S500) | Single dose | 3 |
| | Once a day × 7 days | 2 |
| | Twice a day × 7 days | 8 |

After the last administration, under anesthesia, the mice are placed tracheal incision and are installed instruments for examining the tolerance of the trachea. Methacholine (MCh) aerosol is used to stimulate the contraction of tracheal and SCIREQ FlexiVent. machine is used to exam the tolerance of trachea of lung.

The following embodiments is that after mixing each components, the mixture is solved in excipient systems of hydrofluoroalkane, directly filled in capsules or is proceed into dry powder inhalation which is administered by a single dose inhalers.

Embodiment 1

| Procaterol HCl | 0.014% | W/W % |
|---|---|---|
| Budesonide | 0.571% | W/W % |
| HFA 227 | 98.664% | W/W % |
| Ethanol | 0.25% | W/W % |
| PEG 400 | 0.50% | W/W % |
| Tital amount | 100.00% | W/W % |

Embodiment 2

| Procaterol HCl | 0.014% | W/W % |
|---|---|---|
| Fluticasone propionate | 0.286% | W/W % |
| HFA 227 | 98.95% | W/W % |
| Ethanol | 0.25% | W/W % |
| PEG 400 | 0.50% | W/W % |
| Tital amount | 100.00% | W/W % |

Embodiment 3

| Procaterol HCl | 0.014% | W/W % |
|---|---|---|
| Mometasone furoate | 0.071% | W/W % |
| HFA 227 | 99.164% | W/W % |
| Ethanol | 0.25% | W/W % |
| PEG 400 | 0.50% | W/W % |
| Tital amount | 100.00% | W/W % |

Embodiment 4

| Procaterol HCl | 0.014% | W/W % |
|---|---|---|
| Fluticasone furoate | 0.157% | W/W % |
| HFA 227 | 99.079% | W/W % |
| Ethanol | 0.25% | W/W % |
| PEG 400 | 0.50% | W/W % |
| Tital amount | 100.00% | W/W % |

Embodiment 5

| Procaterol HCl | 0.0167% | W/W % |
|---|---|---|
| Budesonide | 0.333% | W/W % |
| HFA 134a | 99.57% | W/W % |
| Ethanol | 1% | W/W % |
| PEG 400 | 1% | W/W % |
| Tital amount | 100.00% | W/W % |

Embodiment 6

| Budesonide | 0.67% | W/W % |
|---|---|---|
| HFA 134a | 99.57% | W/W % |
| Ethanol | 1% | W/W % |
| PEG 400 | 1% | W/W % |
| Tital amount | 100.00% | W/W % |

Embodiment 7

| Fluticasone propionate | 0.417% | W/W % |
|---|---|---|
| HFA 134a | 98.833% | W/W % |
| Ethanol | 0.25% | W/W % |
| PEG 400 | 0.50% | W/W % |
| Tital amount | 100.00% | W/W % |

Embodiment 8

| Procaterol HCl | 0.014% | W/W % |
|---|---|---|
| Ciclesonide | 0.286% | W/W % |
| HFA 227 | 98.95% | W/W % |
| Ethanol | 0.25% | W/W % |
| PEG 400 | 0.50% | W/W % |
| Tital amount | 100.00% | W/W % |

Embodiment 9

| Procaterol HCl | 0.014% | W/W % |
|---|---|---|
| Beclomethasone dipropionate | 0.071% | W/W % |
| HFA 227 | 99.164% | W/W % |
| Ethanol | 0.25% | W/W % |
| PEG 400 | 0.50% | W/W % |
| Tital amount | 100.00% | W/W % |

Embodiment 10

| Procaterol HCl | 0.014% | W/W % |
|---|---|---|
| Beclomethasone dipropionate | 0.143% | W/W % |
| HFA 227 | 99.093% | W/W % |
| Ethanol | 0.25% | W/W % |
| PEG 400 | 0.50% | W/W % |
| Tital amount | 100.00% | W/W % |

Embodiment 11

| Procaterol HCl | 0.014% | W/W % |
|---|---|---|
| Beclomethasone dipropionate | 0.286% | W/W % |
| HFA 227 | 98.95% | W/W % |
| Ethanol | 0.25% | W/W % |
| PEG 400 | 0.50% | W/W % |
| Tital amount | 100.00% | W/W % |

Embodiment 12

| Procaterol HCl | 0.014% | W/W % |
|---|---|---|
| Budesonide | 0.143% | W/W % |
| HFA 227 | 99.093% | W/W % |
| Ethanol | 0.25% | W/W % |
| PEG 400 | 0.50% | W/W % |
| Tital amount | 100.00% | W/W % |

Embodiment 13

| Procaterol HCl | 0.014% | W/W % |
|---|---|---|
| Budesonide | 0.257% | W/W % |
| HFA 227 | 98.98% | W/W % |
| Ethanol | 0.25% | W/W % |
| PEG 400 | 0.50% | W/W % |
| Tital amount | 100.00% | W/W % |

Embodiment 14

| Procaterol HCl | 0.014% | W/W % |
|---|---|---|
| Fluticasone propionate | 0.357% | W/W % |
| HFA 227 | 98.879% | W/W % |
| Ethanol | 0.25% | W/W % |
| PEG 400 | 0.50% | W/W % |
| Tital amount | 100.00% | W/W % |

Embodiment 15

| Procaterol HCl | 0.014% | W/W % |
|---|---|---|
| Fluticasone propionate | 0.071% | W/W % |
| HFA 227 | 99.16% | W/W % |
| Ethanol | 0.25% | W/W % |
| PEG 400 | 0.50% | W/W % |
| Tital amount | 100.00% | W/W % |

Embodiment 16

| Procaterol HCl | 0.014% | W/W % |
|---|---|---|
| Fluticasone furoate | 0.314% | W/W % |
| HFA 227 | 98.921% | W/W % |
| Ethanol | 0.25% | W/W % |
| PEG 400 | 0.50% | W/W % |
| Tital amount | 100.00% | W/W % |

Embodiment 17

| Procaterol HCl | 0.014% | W/W % |
|---|---|---|
| Fluticasone furoate | 0.157% | W/W % |
| HFA 227 | 99.079% | W/W % |
| Ethanol | 0.25% | W/W % |
| PEG 400 | 0.50% | W/W % |
| Tital amount | 100.00% | W/W % |

Embodiment 18

| Procaterol HCl | 2.439% | W/W % |
|---|---|---|
| Budesonide | 97.561% | W/W % |
| Tital amount | 100.00% | W/W % |

Embodiment 19

| Procaterol HCl | 16.667% | W/W % |
|---|---|---|
| Fluticasone propionate | 83.333% | W/W % |
| Tital amount | 100.00% | W/W % |

Embodiment 20

| Procaterol HCl | 9.091% | W/W % |
|---|---|---|
| Beclomethasone dipropionate | 90.909% | W/W % |
| Tital amount | 100.00% | W/W % |

Embodiment 21

| Procaterol HCl | 0.133% | W/W % |
|---|---|---|
| Mometasone fuoate | 1.333% | W/W % |
| Lactose | 98.533% | W/W % |
| Tital amount | 100.00% | W/W % |

Embodiment 22

| Procaterol HCl | 0.133% | W/W % |
|---|---|---|
| Fluticasone fuoate | 2.933% | W/W % |
| Lactose | 96.933% | W/W % |
| Tital amount | 100.00% | W/W % |

Embodiment 23

| Procaterol HCl | 0.133% | W/W % |
|---|---|---|
| Budesonide | 2.667% | W/W % |
| Lactose | 97.200% | W/W % |
| Tital amount | 100.00% | W/W % |

Embodiment 24

| Procaterol HCl | 0.133% | W/W % |
|---|---|---|
| Ciclensonide | 0.667% | W/W % |
| Lactose | 99.200% | W/W % |
| Tital amount | 100.00% | W/W % |

There are further Embodiments are provided as follows:

Embodiment 1: An inhaled composition, characterized by including an effective amount of beta-2 agonist and an effective amount of corticosteroid and optionally a pharmaceutically acceptable carrier when necessary.

Embodiment 2: The composition as described in Embodiment 1, characterized by being used as a reliever for a patient with asthma or chronic obstructive pulmonary disease, or a controller in eccentric way such as before sleeping or after waking up.

Embodiment 3: The composition as described in Embodiment 1 or 2, characterized in that the beta-2 agonist is at least one selected from a group consisting of Albuterol, Fenoterol, Procaterol, Terbutaline, Albuterol sulfate, Procaterol HCl, Fenoterol hydrobromide, and Terbutaline sulphate.

Embodiment 4: The composition as described in any one of Embodiments 1 to 3, characterized in that the corticosteroid is at least one selected from a group consisting of Budesonide, Fluticasone, Mometasone, Ciclesonide, Beclomethasone, Triamcinolone, Fluticasone propionate, Beclomethasone dipropionate, and Triamcinolone Acetonide.

Embodiment 5: The composition as described in any one of Embodiments 1 to 4, characterized in that the ratio of the beta-2 agonist and the corticosteroid is 1:2 w/w % to 1:70 w/w %.

Embodiment 6: An inhaled HFA composition, characterized by comprising: a pharmaceutically acceptable carrier and an effective amount of beta-2 agonist and an effective amount of corticosteroid.

Embodiment 7: The HFA composition as described in Embodiment 6, characterized by being used as a reliever for a patient with asthma or chronic obstructive pulmonary disease, or a controller in eccentric way such as before sleeping or after waking up.

Embodiment 8: The HFA composition as described in Embodiment 6 or 7, characterized in that the beta-2 agonist is at least one selected from a group consisting of Albuterol, Fenoterol, Procaterol, Terbutaline, Albuterol sulfate, Procaterol HCl, Fenoterol hydrobromide, and Terbutaline sulphate.

Embodiment 9: The HFA composition as described in any one of Embodiments 6 to 8, characterized in that the corticosteroid is at least one selected from a group consisting of Budesonide, Fluticasone, Mometasone, Ciclesonide, Beclomethasone, Triamcinolone, Fluticasone propionate, Beclomethasone dipropionate, and Triamcinolone Acetonide.

Embodiment 10: The HFA composition as described in any one of Embodiments 6 to 9, characterized in that the ratio of the beta-2 agonist and the corticosteroid is 1:4 w/w % to 1:50 w/w %.

Embodiment 11: The HFA composition as described in any one of Embodiments 6 to 10, characterized in that the pharmaceutically acceptable carrier is selected from HFA propellant, surfactant, solvent, suspending agent or lactose when necessary.

Embodiment 12: The HFA composition as described in any one of Embodiments 6 to 11, characterized in that the pharmaceutically acceptable carrier is selected from HFA propellant, surfactant, solvent or suspending agent.

Embodiment 13: An inhaled powder composition, characterized by comprising: a pharmaceutically acceptable carrier and an effective amount of beta-2 agonist and an effective amount of corticosteroid.

Embodiment 14: The powder composition as described in Embodiment 13, characterized by being used as a reliever for a patient with asthma or chronic obstructive pulmonary disease, or a controller in eccentric way such as before sleeping or after waking up.

Embodiment 15: The powder composition as described in Embodiment 13 or 14, characterized in that the beta-2 agonist is at least one selected from a group consisting of Albuterol, Fenoterol, Procaterol, Terbutaline, Albuterol sulfate, Procaterol HCl, Fenoterol hydrobromide, and Terbutaline sulphate.

Embodiment 16: The powder composition as described in any one of Embodiments 13 to 15, characterized in that the corticosteroid is at least one selected from a group consisting of Budesonide, Fluticasone, Mometasone, Ciclesonide, Beclomethasone, Triamcinolone, Fluticasone propionate, Beclomethasone dipropionate, and Triamcinolone Acetonide.

Embodiment 17: The powder composition as described in any one of Embodiments 13 to 16, characterized in that the ratio of the beta-2 agonist and the corticosteroid is 1:4 w/w % to 1:50 w/w %.

Embodiment 18: The powder composition as described in any one of Embodiments 13 to 17, characterized in that the pharmaceutically acceptable carrier is selected from lactose when necessary.

Embodiment 19: The composition as described in any one of the above-mentioned Embodiments, characterized in that the beta-2 agonist is Fenoterol, and the corticosteroid is at least one selected from a group consisting of Budesonide, Fluticasone, Mometasone, Ciclesonide, Beclomethasone, Triamcinolone, Fluticasone propionate, Beclomethasone dipropionate, Triamcinolone Acetonide and a combination thereof.

Embodiment 20: The composition as described in any one of the above-mentioned Embodiments, characterized in that the beta-2 agonist is Procaterol, and the corticosteroid is at least one selected from a group consisting of Budesonide, Fluticasone, Mometasone, Ciclesonide, Beclomethasone, Triamcinolone, Fluticasone propionate, Beclomethasone dipropionate, Triamcinolone Acetonide and a combination thereof.

Embodiment 21: The composition as described in any one of the above-mentioned Embodiments, characterized in that the beta-2 agonist is Albuterol, and the corticosteroid is at least one selected from a group consisting of Budesonide, Fluticasone, Mometasone, Ciclesonide, Beclomethasone, Triamcinolone, Fluticasone propionate, Beclomethasone dipropionate, Triamcinolone Acetonide and a combination thereof.

Embodiment 22: The composition as described in any one of the above-mentioned Embodiments, characterized in that the beta-2 agonist is Albuterol sulfate, and the corticosteroid is at least one selected from a group consisting of Budesonide, Fluticasone, Mometasone, Ciclesonide, Beclomethasone, Triamcinolone, Fluticasone propionate, Beclomethasone dipropionate, Triamcinolone Acetonide and a combination thereof.

Embodiment 23: The composition as described in any one of the above-mentioned Embodiments, characterized in that the beta-2 agonist is Procaterol HCl, and the corticosteroid is at least one selected from a group consisting of Budesonide, Fluticasone, Mometasone, Ciclesonide, Beclomethasone, Triamcinolone, Fluticasone propionate, Beclomethasone dipropionate, Triamcinolone Acetonide and a combination thereof.

Embodiment 24: The composition as described in any one of the above-mentioned Embodiments, characterized in that the beta-2 agonist is Fenoterol hydrobromide, and the corticosteroid is at least one selected from a group consisting of Budesonide, Fluticasone, Mometasone, Ciclesonide, Beclomethasone, Triamcinolone, Fluticasone propionate, Beclomethasone dipropionate, Triamcinolone Acetonide and a combination thereof.

Embodiment 25: The composition as described in any one of Embodiments 1 to 12, characterized in that the HFA propellant is selected from HFA 134a or HFA 227.

Embodiment 26: The composition as described in any one of Embodiments 1 to 12, characterized in that the HFA propellant is selected from the combination of HFA 134a and HFA 227.

Although the present invention has been disclosed as the above-mentioned with the preferred embodiments, however, it is not intended to limit the scope of the present invention. Any technical personnel skilled in the art can easily think of the changes or replacements within the disclosed technical scope of the present invention, which should be covered within the protecting scope of the present invention. Accordingly, the protecting scope of the present invention should be in accordance with the protecting scope of the claims.

What is claimed is:

1. An inhaled composition, characterized by comprising:
   an effective amount of inhaled Procaterol; and
   an effective amount of inhaled Budesonide;
   wherein the ratio of the inhaled Procaterol and the inhaled Budesonide is 1:5 w/w % to 1:60 w/w %.

2. The inhaled composition as claimed in claim 1, further comprising a pharmaceutically acceptable carrier.

3. The inhaled composition as claimed in claim 1, wherein the inhaled composition is an inhaled aerosol composition.

4. The inhaled composition as claimed in claim 1, wherein the inhaled composition further comprises a propellant and is suitable for use in a metered dose inhaler.

5. The inhaled composition as claimed in claim 1, wherein the inhaled composition is a dry powder and is suitable for use in a dry powder inhaler.

6. A method of relieving asthma or obstructive respiratory disorder comprising administering an effective amount of an inhaled composition of claim 1 to a subject.

7. The method as claimed in claim 6, wherein the inhaled composition further comprises a pharmaceutically acceptable carrier.

8. The method as claimed in claim 6, wherein the inhaled composition is an inhaled aerosol composition.

* * * * *